US006918901B1

(12) United States Patent
Theeuwes et al.

(10) Patent No.: US 6,918,901 B1
(45) Date of Patent: Jul. 19, 2005

(54) DEVICE AND METHOD FOR ENHANCING TRANSDERMAL AGENT FLUX

(76) Inventors: Felix Theeuwes, 27350 Altamont Rd., Los Altos Hills, CA (US) 94023; Michel J. N. Cormier, 278 Andsbury Ave., Mountain View, CA (US) 94043; Armand P. Neukermans, 3510 Arbutus Ave., Palo Alto, CA (US) 94303

( * ) Notice: Subject to any disclaimer, the term of this patent is extended or adjusted under 35 U.S.C. 154(b) by 306 days.

(21) Appl. No.: 08/988,292

(22) Filed: Dec. 10, 1997

(51) Int. Cl.[7] .............................................. A61M 31/00

(52) U.S. Cl. ........................ 604/500; 604/20; 604/272; 604/501; 604/22; 604/892.1; 600/573; 600/583; 600/309

(58) Field of Search .............................. 604/20, 46, 47, 604/500, 272, 501, 22; 132/207, 108–110, 132/221; 600/573, 583, 309

(56) References Cited

U.S. PATENT DOCUMENTS 2,609,821 A * 9/1952 Weissberger ................. 132/13
2,922,425 A * 1/1960 Lerner et al. .................. 132/9
3,675,766 A 7/1972 Rosenthal .................. 206/63.4
3,814,097 A 6/1974 Ganderton et al. ......... 128/260
3,964,482 A 6/1976 Gerstel et al. .............. 128/260
4,340,048 A 7/1982 Eckenhoff ............... 128/213 R
4,379,454 A 4/1983 Campbell et al. ........... 604/897
4,588,580 A 5/1986 Gale et al. .................... 424/21
4,655,766 A 4/1987 Theeuwes et al. .......... 604/896
4,698,062 A 10/1987 Gale et al. .................. 604/896
4,711,247 A 12/1987 Fishman ..................... 128/743
4,753,651 A 6/1988 Eckenhoff ................... 424/449
4,832,953 A 5/1989 Campbell et al. ........... 424/448
4,856,541 A * 8/1989 Kellett et al. ............... 132/110
4,867,982 A 9/1989 Campbell et al. ........... 424/449
5,002,075 A * 3/1991 Kellett et al. ............... 132/108
5,080,646 A 1/1992 Theeuwes et al. ............ 604/20
5,147,296 A 9/1992 Theeuwes et al. ............ 604/20
5,169,382 A 12/1992 Theeuwes et al. ............ 604/20
5,169,383 A 12/1992 Gyory et al. ................. 604/20
5,224,927 A * 7/1993 Tapper ........................ 604/20
5,242,406 A 9/1993 Gross et al. ................ 604/132
5,250,023 A 10/1993 Lee et al. ...................... 604/20
5,261,426 A * 11/1993 Kellett et al. ............... 132/108
5,268,209 A 12/1993 Hunt et al. ................ 428/34.3
5,279,544 A * 1/1994 Gross et al. .................. 604/20
5,310,404 A 5/1994 Gyory et al. ................. 604/20
5,385,543 A 1/1995 Haak et al. ................... 604/20
5,423,739 A 6/1995 Phipps et al. ................. 604/20
5,472,456 A * 12/1995 Larsky et al. .................. 8/405
5,845,653 A * 12/1998 Abercrombie ............. 132/208

FOREIGN PATENT DOCUMENTS

DE 195 25 607 A1 1/1997

(Continued)

OTHER PUBLICATIONS

Reiss, Susan M., Biophotonics Internationalm May/Jun. 1997, pp 43-45, "Glucose- and Blood- Monitoring Systems View for Top Spot."

(Continued)

*Primary Examiner*—Cris L. Rodriguez
(74) *Attorney, Agent, or Firm*—Francis Law Group

(57) ABSTRACT

An agent delivery or sampling device (2) comprising a member (6) having a plurality of blades (4) for piercing the skin and a connecting medium (65) covering at least a part of the skin contacting side (48) of the member (6) for increasing transdermal flux of an agent.

6 Claims, 4 Drawing Sheets

FOREIGN PATENT DOCUMENTS

| | | | |
|---|---|---|---|
| EP | 0 429 842 A2 | 6/1991 | |
| WO | WO 96/17648 | 6/1996 | ............ A61N 1/30 |
| WO | WO 96/27155 | 11/1996 | |
| WO | WO 96/37256 | 11/1996 | |
| WO | WO 97/07734 | 3/1997 | ............ A51B 5/00 |

OTHER PUBLICATIONS

Eppstein, Jonathan, et al., "Rapid Transdermal Drug Delivery with Thermal Micro-Poration," presented at a transdermal delivery conference in San Diego on Dec. 15-18, 1997 and sponsored by IBC.

* cited by examiner

DEVICE AND METHOD FOR ENHANCING TRANSDERMAL AGENT FLUX

TECHNICAL FIELD

The present invention relates to transdermal agent delivery and sampling. More particularly, this invention relates to the transdermal delivery of agents, such as peptides and proteins, through the skin of an animal, as well as the transdermal sampling of agents, such as glucose, electrolyte and substances of abuse, such as but not limited to alcohol and illicit drugs.

BACKGROUND ART

Interest in the percutaneous or transdermal delivery of peptides and proteins to the human body continues to grow with the increasing number of medically useful peptides and proteins becoming available in large quantities and pure form. The transdermal delivery of peptides and proteins still faces significant problems. In many instances, the rate of delivery or flux of polypeptides through the skin is insufficient to produce a desired therapeutic effect due to the low flux of polypeptides through skin. In addition, polypeptides and proteins are easily degradable during and after penetration of the skin, prior to reaching target cells. Likewise, the passive flux of water soluble small molecules such as salts is limited.

One method of increasing the transdermal delivery of agents relies on the application of an electric current across the body surface or on "electrotransport". "Electrotransport" refers generally to the passage of a beneficial agent, e.g., a drug or drug precursor, through a body surface such as skin, mucous membranes, nails, and the like. The transport of the agent is induced or enhanced by the application of an electrical potential, which results in the application of electric current, which delivers or enhances delivery of the agent. The electrotransport of agents through a body surface may be attained in various manners. One widely used electrotransport process, iontophoresis, involves the electrically induced transport of charged ions. Electroosmosis, another type of electrotransport process, involves the movement of a solvent with the agent through a membrane under the influence of an electric field. Electroporation, still another type of electrotransport, involves the passage of an agent through pores formed by applying a high voltage electrical pulse to a membrane. In many instances, more than one of these processes may be occurring simultaneously to different extents. Accordingly, the term "electrotransport" is given herein its broadest possible interpretation, to include the electrically induced or enhanced transport of at least one charged or uncharged agent, or mixtures thereof, regardless of the specific mechanism(s) by which the agent is actually being transported. Electrotransport delivery generally increases agent delivery, particularly peptide delivery rates, relative to passive or non-electrically assisted transdermal delivery. However, further increases in transdermal delivery rates and reductions in peptide degradation during transdermal delivery are highly desirable.

One method of increasing the agent transdermal delivery rate involves pre-treating the skin with, or alternatively co-delivering with the beneficial agent, a skin permeation enhancer. The term "permeation enhancer" is broadly used herein to describe a substance which, when applied to a body surface through which the agent is delivered, enhances its flux therethrough. The mechanism may involve a reduction of the electrical resistance of the body surface to the passage of the agent therethrough, an increase in the permeability of the body surface, the creation of hydrophilic pathways through the body surface, and/or a reduction in the degradation of the agent (e.g., degradation by skin enzymes) during electrotransport.

There have been many mechanical attempts to enhance transdermal flux, such as, U.S. Pat. No. 5,279,544 issued to Gross et al., U.S. Pat. No. 5,250,023 issued to Lee et al., and U.S. Pat. No. 3,964,482 issued to Gerstel et al. These devices utilize tubular or cylindrical structures generally, although Gerstel does disclose the use of other shapes, to pierce the outer layer of the skin. Each of these devices provide manufacturing challenges, limited mechanical attachment of the structure to the skin, undesirable irritation to the skin, and/or limited conductive contact with the skin.

DESCRIPTION OF THE INVENTION

The present invention is a high volume producable, low-cost device suitable for increasing transdermal flux with skin piercing protrusions and contacting a body surface over a large contact area to reduce skin irritation and enhance agent delivery or sampling. The device of the present invention pierces the stratum corneum of a body surface to form pathways through which a substance can either be introduced (i.e., delivery) or withdrawn (i.e., sampling). In one aspect, the invention comprises a plurality of protrusions for piercing the skin which extend through a connecting medium. The connecting medium assists in making substantial contact with the body surface for either delivering or sampling an agent. For an electrotransport device, the connecting medium spreads out the contact area to all the protrusions to reduce the current density at particular locations to reduce irritation.

In one aspect of the invention, the device utilizes a member having a plurality of openings therethrough, a plurality of blades integral therewith and extending downward from a first side of the member, and a connecting medium covering at least a part of the first side of the member. The device of the present invention can be used in connection with agent delivery, agent sampling or both. Delivery devices for use with the present invention include, but are not limited to, electrotransport devices, passive devices, osmotic devices and pressure driven devices. Sampling devices for use with the present invention include, but are not limited to, reverse electrotransport devices, passive devices, and osmotic devices.

MODES FOR CARRYING OUT THE INVENTION

Figure 1:
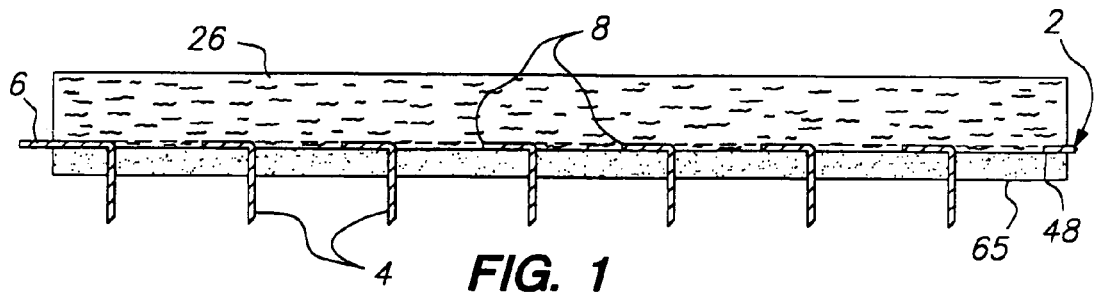
FIG. 1 is an enlarged cross-sectional view of a skin piercing device in accordance with the present invention.

Turning now to the drawings in detail, the skin piercing device 2 of the present invention is generally shown in FIG. 1. Device 2 is used for the percutaneous administration or sampling of an agent. The terms "substance", "agent" and "drug" are used interchangeably herein and broadly include physiologically or pharmacologically active substances for producing a localized or systemic effect or effects in mammals including humans and primates, avians, valuable domestic household, sport or farm animals, or for administering to laboratory animals such as mice, rats, guinea pigs, and the like. These terms also include substances such as glucose, electrolyte, alcohol, illicit drugs, etc. that can be sampled through the skin. The major barrier properties of the skin, such as resistance to agent conduction, reside with the outer layer (i.e., stratum corneum). The inner division of the epidermis generally comprises three layers commonly identified as stratum granulosum, stratum malpighii, and stratum germinativum. There is essentially little or no resistance to conduction or to absorption of an agent through the stratum granulosum, stratum malpighii, and stratum germinativum. The device of the present invention is used to pierce the stratum corneum for improved delivery or sampling of an agent and to make contact with the skin over a large contact area using a connecting medium 65 (FIG. 1).

The connecting medium 65 of the present invention is predisposed on the skin contacting side 48 of the agent delivery or sampling device. In one embodiment, the connecting medium 65 is a conduit for the agent and acts as a bridge between the agent containing or collecting reservoir 26 and the skin, thus allowing an agent to be transported unhindered therethrough. The connecting medium can be free of agent or preloaded with agent. In the embodiment of FIG. 1, the reservoir 26 is illustrated as being separate from the connecting medium 65. It should be appreciated, however, that in some embodiments there will be migration of agent into the connecting medium prior to use of the device such that the reservoir and connecting medium are not discrete, for example, the matrix in the reservoir and the connecting medium can be the same material. In addition, a separate reservoir may not be present in that the connecting medium 65 may be the reservoir for the sampled agent or the agent to be delivered. In other words, the connecting medium is capable of storing the agent to be delivered or the sampled agent. The connecting medium is typically in the range of about 10 microns to about 100 microns thick.

The connecting medium 65 is either fabricated and stored dry which can be rehydrated upon use or can be packaged in the hydrated form. In a preferred embodiment, the connecting medium is an ion conducting hydrogel of a pharmaceutically acceptable grade with minimum extractable or degradation products which sorbs or contains in a functional state an amount of water in the range from 20% to 90%, preferably in the range from 30% to 70%. Preferably the connecting medium is a hydrogel that is at least slightly crosslinked to prevent fragments of polymers from penetrating the skin and has adhesive or tacky properties.

The connecting medium 65 can be any of a large variety of materials as discussed above and further including, by way of example, an organic polymer having at least some pendent substituents capable of being ionic, a polar natural material, a semi-synthetic material, a cellulosic derivative, an alginate derivative, a starch derivative, a dextran, a polysaccharide, a hydrogel polymer having a backbone selected from the group consisting of a hydrous-gelled, linear polyolefin, polycarbonate, polyester, polyether, polyurethane and polyepoxide backbone, with backbone substituents selected from the group consisting of (alkyl, aryl or aralkyl) alcohol, amide, ketone, nitrogen heterocycle or ester pendent substituents, and any combination thereof. The connecting medium can be in a variety of forms such as a gel, solid, hydrogel, powder, liquid, viscous fluid, gauze made of cotton or other absorbent fabrics as well as pads and sponges, both natural and synthetic, may be used. Any suitable materials listed in U.S. Pat. No. 5,385,543 could be used in conjunction with the present invention. U.S. Pat. No. 5,423,739, issued to Phipps et al., describes iontophoretic materials and substances that can be used as the connecting medium.

Figure 2:
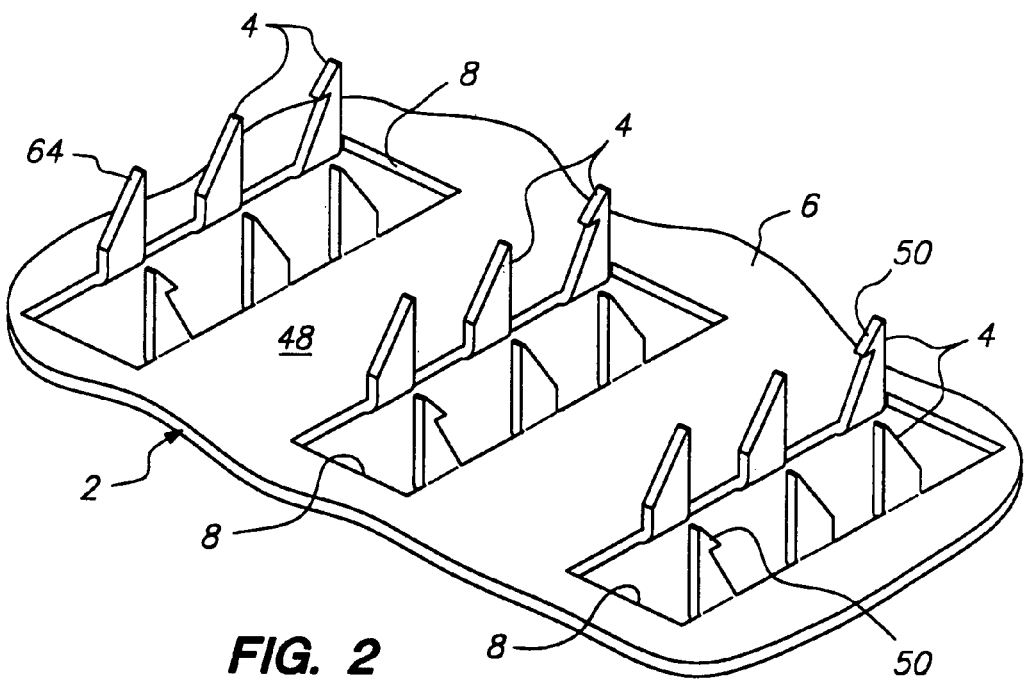
FIG. 2 is an enlarged perspective view of the bottom side of a skin piercing device with a connecting medium removed therefrom for clarity in accordance with one embodiment of the present invention.
Figure 4:
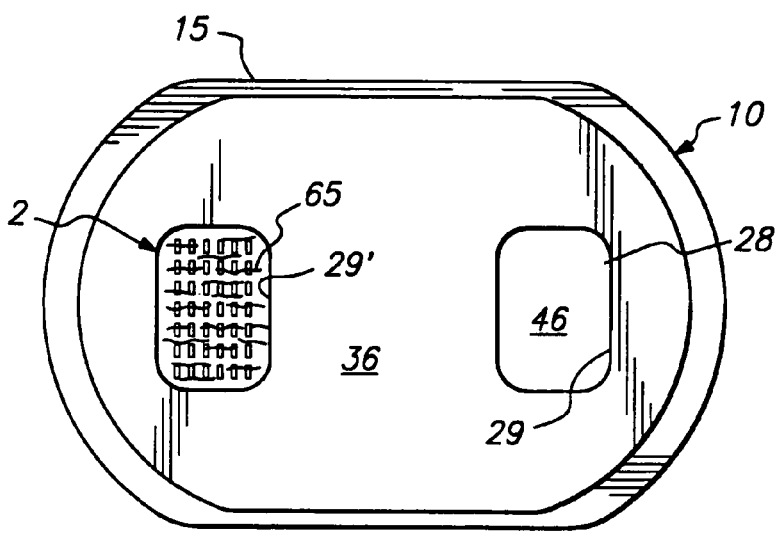
FIG. 4 is a bottom plan view of the electrotransport agent delivery system of FIG. 3.
Figure 3:
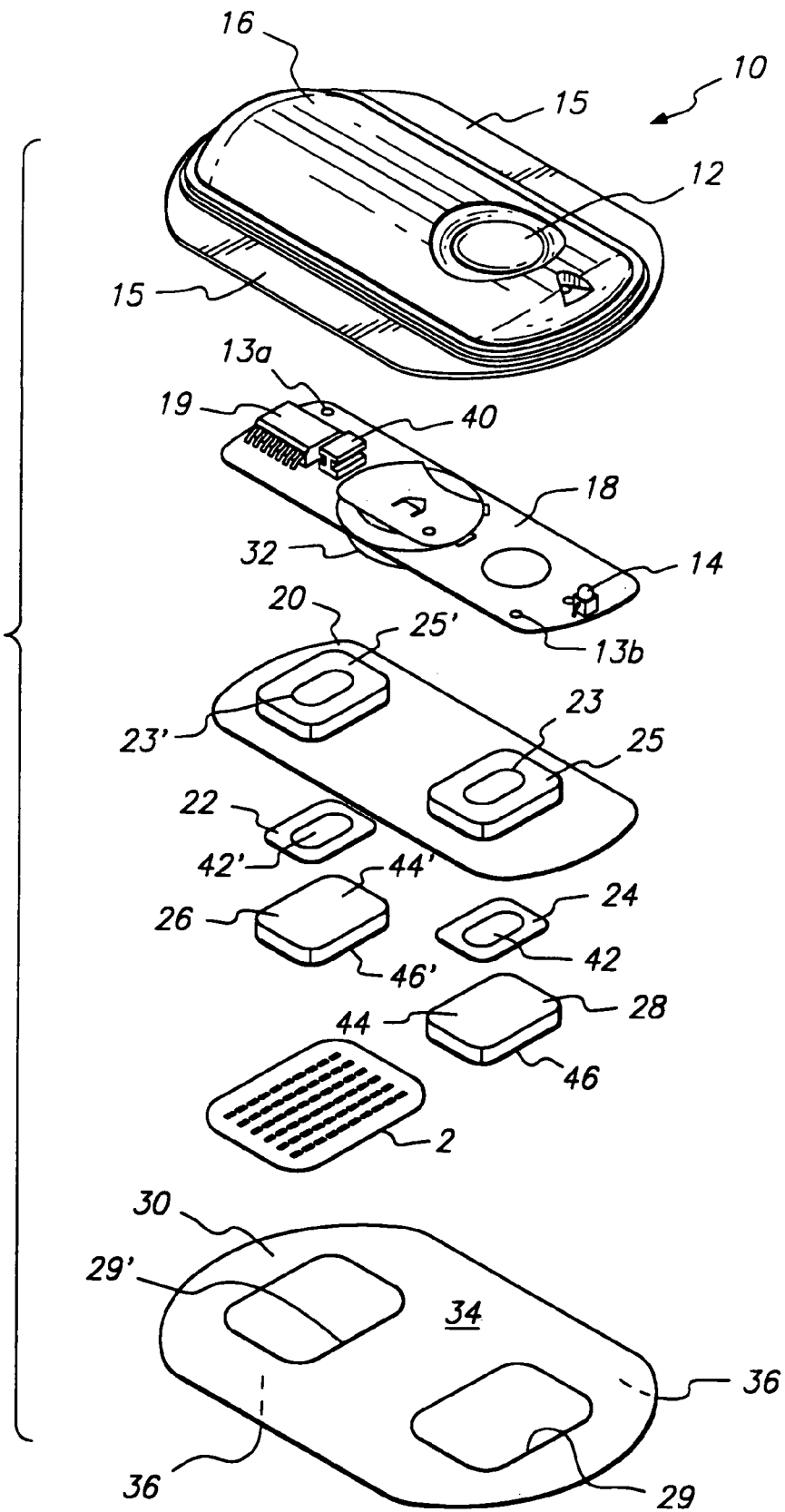
FIG. 3 is a exploded perspective view of one embodiment of an electrotransport agent delivery system according to one embodiment of the present invention.
Figure 5:
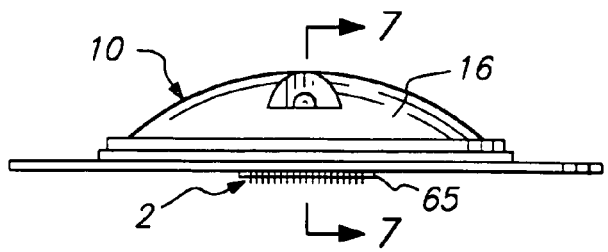
FIG. 5 is a right side elevational view of the electrotransport agent delivery system of FIG. 3.
Figure 6:
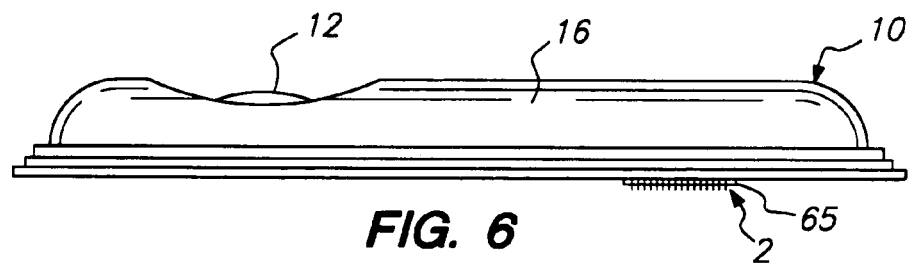
FIG. 6 is a rear elevational view of the electrotransport agent delivery system of FIG. 3.
Figure 7:
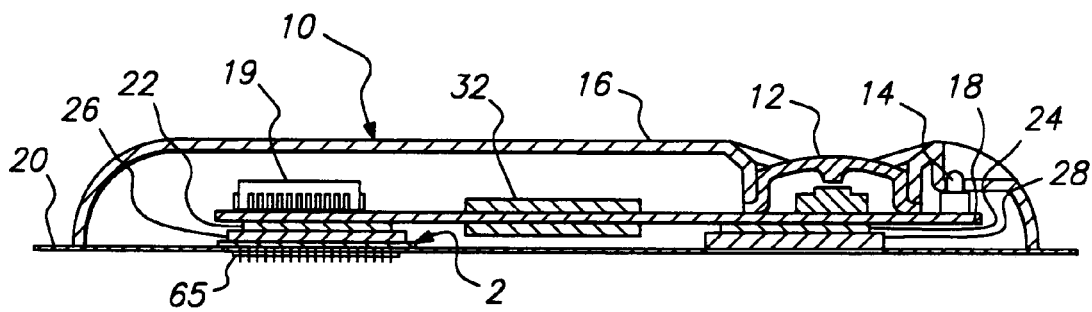
FIG. 7 is a cross-sectional view taken along line 7—7 of the assembled electrotransport agent delivery system of FIG. 5.

Device 2 comprises a plurality of protrusions 4 extending downward from one surface of a member or plate 6 which has a connecting medium 65 (FIG. 1) on at least a portion of surface 48 (see FIG. 2 in which device 2 is in an inverted position to show the protrusions and wherein the connecting medium is removed for clarity). The protrusions 4 can be blades (FIGS. 1 and 2), pins (not shown), or any of a variety of configurations for piercing the skin or body surface. The protrusions 4 penetrate the stratum corneum of the epidermis when pressure is applied to the device to increase the administration of or sampling of a substance through a body surface. The term "body surface" as used herein refers generally to the skin, mucous membranes, and nails of an animal or human, and to the outer surface of a plant. The protrusions 4 extend through the connecting medium 65 to pierce the body surface to create good agent conduction from the system into the body, or vice versa. The member 6 is formed with an opening 8 between the blades 4 for enhancing the movement of agent released from or collected in the agent containing or collecting reservoir 26. In one embodiment, the opening 8 corresponds to the portion of the member occupied by each of the blades 4 prior to the blades being bent into a position which is substantially perpendicular to the plane of member 6. The number of openings per device and the number of blades per device are independent. In addition, the device may have only one large opening with a plurality of blades around the opening. The agent can be administered or sampled at a controlled rate of release from or collection in the reservoir 26 through an agent rate controlling material such as a flux control membrane (not shown) positioned between the reservoir 26 and the member 6.

The protrusions or blades 4 are generally formed from a single piece of material and are sufficiently sharp and long for puncturing at least the stratum corneum of the skin. In one embodiment, the blades 4 and the member 6 are essentially impermeable or are impermeable to the passage of an agent. The width of each blade can be any of a range of widths. The blades 4 can have slanted (i.e., angled) leading edges 64 (FIG. 2) to further reduce the insertion force required to press the blades into the skin tissue. The leading edges of each blade can be all be the same angle or can be at different angles suitable for piercing the skin. Alternatively, the leading edge of each blade can be arcuate (i.e., curved) in shape, having, for example, a convex or concave shape.

The device 2 of the present invention improves the attachment of the device to the skin so that a continuous agent conducting pathway through the body surface is preserved during movement of the body surface. In the embodiment shown in FIG. 2, projections in the form of barbs 50 on at least one of the blades 4 assist in anchoring the device 2 and any corresponding device or structure used in combination therewith to the skin. Barbs 50 can be on any number of the blades from one blade to all blades. The barbs 50 are optional as other means for holding the device in contact with the skin can be used. The present invention can be used in conjunction with a wide variety of blade configurations, for example reference may be had to U.S. Provisional Application No. 60/019,990 filed Jun. 18, 1996 of which any of the disclosed configurations can be used with the present invention.

The pattern for any of the blade array devices 2 of the present invention can be produced with a photo-etching process. A thin member 6 of metal such as stainless steel or titanium is etched photo-lithographically with patterns containing blade-like structures. In general, a thin laminate dry resist or wet resist is applied on the member 6 which typically has a thickness of about 7 micrometers to about 100 micrometers, preferably about 25 micrometers to about 50 micrometers. The resist is contact exposed using a mask having the desired pattern and is subsequently developed. These operations are conducted in much the same way that they are for the manufacture of a printed circuit board. The member 6 is then etched using acidic solutions. After the pattern has been etched through the member, the member 6 is placed on a die having a plurality of openings corresponding to the openings 8 in the member. A punch having a plurality of protrusions corresponding to the openings 8 in the member 6 and openings in the die is initially located above the member and the die. At the initial stage, the blades 4 are in the same plane as the rest of the member 6. The protrusions on the punch are then pressed into the openings, thus bending the blades downward to be substantially perpendicular to the plane of the member 6. The finished structure provides blades 4 with an adjacent opening 8 for the passage of a substance therethrough when the device 2 is applied to the body surface. Rectangular openings 8 are shown in the figures but the invention encompasses the use of any shape openings including, but not limited to, square, triangular, circular and elliptical.

In one embodiment of the etching process, a dry resist (e.g., "Dynachem FL" available from Dynachem located in Tustin, Calif. is applied 12.5 micrometers thick to one or both sides of the member 6 and exposed in a standard manner. Then using a suitable spray etcher (e.g., "Dynamil VRP 10/NM" available from Western Tech. Assoc. located in Anaheim, Calif.) a mixture of ferric chloride and hydrochloric acid is sprayed onto the resist and member 6 at 125 degrees F. for two minutes. A standard caustic stripper is used for the resist removal.

In another embodiment of the etching process, a wet resist (e.g., "Shipley 111S" available from Shipley Corporation, located in Marlborough, Mass.) is applied 7.5 micrometers thick at about 70 degrees F. to one or both sides of the member 6 and exposed in a standard manner. Then a suitable etchant (e.g., ferric chloride) is sprayed onto the resist and member at 120 degrees F. A standard caustic stripper is used for the resist removal.

Generally, the blades 4 are at an angle of about 90 degrees to the surface 48 of the member 6 after being punched, but they can be disposed at any angle forward or backward from the perpendicular position that will facilitate penetration of and attachment to the stratum corneum. In addition, other anchoring elements such as barbs, openings, etc. can be used with the angled blades to further enhance anchoring of the device.

The member 6 and blades 4 can be made from materials that have sufficient strength and manufacturability to produce blades, such as, glasses, ceramics, rigid polymers, metals and metal alloys. Examples of metals and metal alloys include but are not limited to stainless steel, iron, steel, tin, zinc, copper, silver, platinum, aluminum, germanium, nickel, zirconium, titanium and titanium alloys having nickel, molybdenum or chromium. Each of the member and blades can have a thin layer of silver, gold, platinum, iridium, titanium, rhodium plating or evaporated or sputtered biocompatible metals to provide for inertness, biocompatibility and preservation of the sharpness of the edges during storage. An example of glasses include a devitrified glass such as "Photoceram" available from Corning in Corning, N.Y. Examples of polymers include but are not limited to polystyrene, polymethylmethocrylate, polypropylene, "Bakelite", celluloseacetate, ethylceululose, styrene/acrylonitrile copolymers, stryrene/butadiene copolymers, acrylonitrile/butadiene/styrene (ABS) copolymers, polyvinyl chloride and acrylic acid polymers including polyacrylates and polymethacrylates.

The number of blades 4 and openings 8 of any of the embodiments of the device 2 is variable with respect to the desired flux rate, agent being sampled or delivered, delivery or sampling device used (i.e., electrotransport, passive, osmotic, pressure driven, etc.), and other factors as will be evident to one of ordinary skill in the art. In general, the larger the number of blades per unit area (i.e., blade density), the more uniform the flux of the agent is through the skin because there are a greater number of pathways through the skin. Consequently, the smaller the number of blades per unit area, the more concentrated the flux of the agent is through the skin because there are fewer pathways. Higher concentrations of agents in a skin pathway typically lead to higher incidences and/or severity of skin reactions (e.g., irritation). Therefore, larger blade densities reduce the incidence and/or severity of skin reactions.

One embodiment of the present invention relies on the application of an electric current across the body surface or "electrotransport". It will be appreciated by those working in the field that the present invention can be used in conjunction with a wide variety of electrotransport systems, as the invention is not limited in any way in this regard. For examples of electrotransport systems, reference may be had to U.S. Pat. No. 5,147,296 to Theeuwes et al., U.S. Pat. No. 5,080,646 to Theeuwes et al., U.S. Pat. No. 5,169,382 to Theeuwes et al., U.S. Pat. No. 5,423,739 to Phipps et al., U.S. Pat. No. 5,385,543 to Haak et al., U.S. Pat. No. 5,310,404 to Gyory et al., and U.S. Pat. No. 5,169,383 to Gyory et al., of which any of the disclosed electrotransport systems can be used with the present invention.

FIGS. 3–7 illustrate a representative electrotransport delivery device 10 that may be used in conjunction with the present invention. Device 10 comprises an upper housing 16, a circuit board assembly 18, a lower housing 20, anode electrode 22, cathode electrode 24, anode reservoir 26, cathode reservoir 28 and skin-compatible adhesive 30. Upper housing 16 has lateral wings 15 which assist in holding device 10 on a patient's skin. Printed circuit board assembly 18 comprises an integrated circuit 19 coupled to discrete components 40 and battery 32. Circuit board assembly 18 is attached to housing 16 by posts (not shown in FIG. 3) passing through openings 13a and 13b, the ends of the posts being heated/melted in order to heat stake the circuit board assembly 18 to the housing 16. Lower housing 20 is attached to the upper housing 16 by means of adhesive layer 30, the upper surface 34 of adhesive layer 30 being adhered to both lower housing 20 and upper housing 16 including the bottom surfaces of wings 15. Shown (partially) on the underside of circuit board assembly 18 is a button cell battery 32. Other types of batteries may also be employed to power device 10 depending on the need.

The device 10 is generally comprised of battery 32, electronic circuitry 19,40, electrodes 22,24, agent reservoirs 26,28, and skin piercing device 2, all of which are integrated into a self-contained unit. Electrodes 22,24 and reservoirs 26,28 are retained by lower housing 20. Anodic electrode 22 is preferably comprised of a metal such as silver and cathodic electrode 24 is preferably comprised of a metal halide such as silver chloride. The outputs (not shown in FIG. 3) of the circuit board assembly 18 make electrical contact with the electrodes 24 and 22 through openings 23,23' in the depressions 25,25' formed in lower housing 20, by means of electrically conductive adhesive strips 42,42'. Electrodes 22 and 24, in turn, are in direct mechanical and electrical contact with the top sides 44',44 of agent reservoirs 26 and 28. The bottom side 46 of agent reservoir 28 contacts the patient's skin through the opening 29 in adhesive layer 30. The bottom side 46' of agent reservoir 26 contacts the connecting medium through the plurality of openings 8 in the skin piercing device 2. The agent in reservoir 26 is typically a viscous gel that fills the openings 8 such that the agent reservoir is in contact with the connecting medium 65 as can be seen in FIG. 1. As discussed above, typically the agent is present initially in both the reservoir and the connecting medium because of diffusion or because the reservoir and connecting medium are the same material. Both reservoirs 26 and 28 are preferably comprised of polymeric gel materials. A liquid agent solution or suspension is contained in at least one of the reservoirs 26 and 28.

The device 10 adheres to the patient's body surface (e.g., skin) by means of an adhesive layer 30 (which has upper adhesive side 34 and body-contacting adhesive side 36) and, optionally, anchoring elements on the device 2 of any of the embodiments discussed herein. Further, optionally, the connecting medium 65 can be tacky or adhesive for assisting in maintaining contact with the skin. The adhesive side 36 covers the entire underneath side of the device 10 except where the device 2 and cathodic electrode are located. The adhesive side 36 has adhesive properties which assures that the device 10 remains in place on the body during normal user activity, and yet permits reasonable removal after the predetermined (e.g., 24-hour) wear period. Upper adhesive side 34 adheres to lower housing 20 and retains the electrodes and agent reservoirs within housing depression 25, 25' as well as retains device 2 to lower housing 20 and lower housing 20 to upper housing 16.

In one embodiment of the agent delivery device there is a release liner (not shown) on the device 10 for maintaining the integrity of the device when it is not in use. In use, the release liner is stripped from the device before the device is applied to the skin. Device 10 also has a push button switch 12, which when pressed turns the device 10 on which is made apparent to the user by means of LED 14 becoming lit. Drug is delivered through the patient's skin (e.g., on the arm) by electrotransport over the predetermined delivery interval.

Examples of neutral or uncharged hydrogels for use in the electrotransport system are polyvinyl alcohol crosslinked through a heating or cooling crystallization process or a combination of polyox crosslinked with carbopol or polyacrylic acid. The connecting medium can be electrically charged such as an ion exchange resin with a fixed charge and mobile counter charges. A preferred embodiment is a resin with fixed charges opposite the charge of the agent ion. An example of an ionically charged or ion exchange resin is cholestyramine®.

In other embodiments of the present invention, passive transdermal delivery or sampling devices are used with a connecting medium 65 predisposed on the bottom (i.e., skin facing) surface of the device. It will be appreciated by those working in the field that the present invention can be used in conjunction with a wide variety of passive transdermal systems, as the invention is not limited in this regard. For examples of passive systems, reference may be had to, but not limited to, U.S. Pat. No. 4,379,454 to Campbell et al., U.S. Pat. No. 4,588,580 to Gale et al., U.S. Pat. No. 4,832,953 to Campbell et al., U.S. Pat. No. 4,698,062 to Gale et al., U.S. Pat. No. 4,867,982 to Campbell et al., and U.S. Pat. No. 5,268,209 to Hunt at al., of which any of the disclosed systems can be used with the present invention. Two examples of passive transdermal delivery devices are illustrated in FIGS. 8 and 9.

Figure 8:
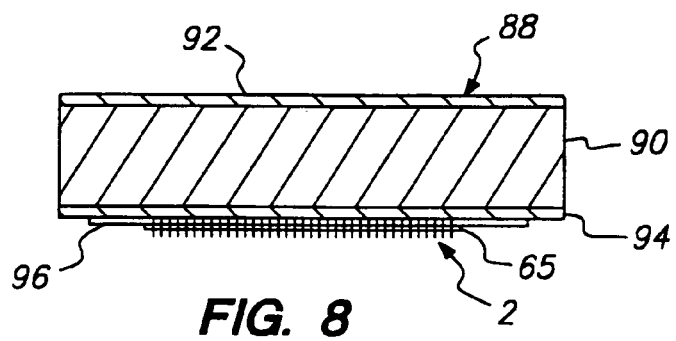
FIG. 8 is a diagrammatic cross-sectional view of a passive agent delivery system in accordance with one embodiment of the present invention.

In FIG. 8, passive transdermal delivery device 88 comprises a reservoir 90 containing a therapeutic agent (e.g., a drug) to be delivered transdermally. Reservoir 90 is preferably in the form of a matrix containing the agent dispersed therein. Reservoir 90 is sandwiched between a backing layer 92, which is impermeable to the agent, and an optional rate-controlling membrane 94. In FIG. 8, the reservoir 90 is formed of a material, such as a polymer, that is sufficiently viscous to maintain its shape. If a lower viscosity material is used for reservoir 90, such as an aqueous gel, backing layer 92 and rate-controlling membrane 94 would be sealed together about their periphery to prevent leakage. Located below membrane 94 is skin piercing device 2 with connecting medium 65 on a skin facing surface thereof which extends through the openings (not shown) in device 2 to contact membrane 94. The device 88 adheres to a body surface by means of contact adhesive layer 96 around the periphery of the device 2 and, optionally, by the anchoring elements of any of the embodiments described previously. In most instances, the connecting medium 65 will initially contain agent. A strippable release liner (not shown) is normally provided along the exposed surface of adhesive layer 96 and is removed prior to application of device 10 to the body surface.

Figure 9:
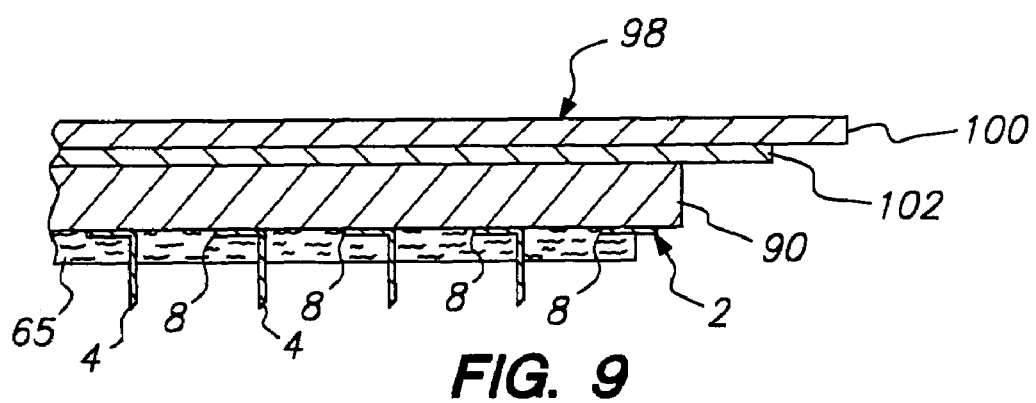
FIG. 9 is a diagrammatic cross-sectional view of another embodiment of a passive agent delivery system in accordance with the present invention.

Alternatively, as shown in enlarged FIG. 9, transdermal therapeutic device 98 may be attached to a body surface by means of a flexible adhesive overlay 100. Device 98 is comprised of an agent-containing reservoir 90 which is preferably in the form of a matrix containing the agent dispersed therein. Connecting medium 65 extends through the openings 8 to contact the reservoir 90. Alternatively, the matrix in reservoir 90 can extend through the openings 8 initially to be in contact with the connecting medium 65 or the reservoir and connecting medium can be the same. An impermeable backing layer 102 is provided adjacent one surface of reservoir 90. Adhesive overlay 100 maintains the device on the body surface. Adhesive overly 100 can be fabricated together with, or provided separately from, the remaining elements of the device 98. With certain formulations, the adhesive overlay 100 may be preferable to the contact adhesive 96 shown in FIG. 8. This is true, for example, where the agent reservoir contains a material (such as, for example, an oily surfactant) which adversely affects the adhesive properties of the contact adhesive layer 96. Impermeable backing layer 102 is preferably slightly larger than reservoir 90, and in this manner prevents the agents in reservoir 90 from adversely interacting with the adhesive in overlay 100. Optionally, a rate-controlling membrane (not shown in FIG. 9) similar to membrane 94 in FIG. 8 can be provided on the body surface side of reservoir 90. A strippable release liner (not shown) is also normally provided with device 98 and is removed just prior to application of device 98 to the body surface.

The formulation of reservoir 90 may be aqueous or nonaqueous based. The formulation is designed to deliver the agent at the necessary fluxes. Aqueous formulations typically comprise water and about 1 to 60 weight percent of a hydrophilic polymer as a gelling agent, such as hydroxyethylcellulose, hydroxypropylcellulose, hydroxyethylmethacrylate and polymers used in soft contact lenses. Typical non-aqueous formulations are comprised of silicone fluid, silicone rubbers, hydrocarbon polymers, polyisobutylene, rubbers, or mineral oil. Mineral oil-based gels also typically contain 1 to 2 weight percent of a gelling agent such as colloidal silicon dioxide.

The reservoir matrix having agent therein should be compatible with the delivered agent, uptake inhibiting agent (if any) and any carrier therefore. When using an aqueous-based system, the reservoir matrix is preferably a hydrophilic polymer (e.g., a hydrogel). When using a non-aqueous-based system, the reservoir matrix is preferably composed of a hydrophobic polymer. Suitable polymeric matrices are well known in the transdermal drug delivery art.

When a constant agent delivery rate is desired, the agent is present in the matrix or carrier at a concentration in excess of saturation, the amount of excess being a function of the desired length of the agent delivery period of the system. The agent may, however, be present at a level below saturation without departing from this invention as long as the agent and the uptake-inhibiting agent (if any) are continuously and co-extensively administered to the same body surface site in an amount and for a period of time sufficient to reduce or eliminate skin irritation by the agent.

In addition to the agent, the connecting medium may also contain dyes, pigments, inert fillers, permeation enhancers, excipients tackifiers, neutral polymers, surfactants, reagents, buffers, plasticizers, and other conventional components of pharmaceutical products or transdermal devices known in the art.

The amount of agent present in the reservoir and the size of the reservoir is generally non-limited and is an amount equal to or larger than the amount of agent that in its released form is effective in bringing about the desired local and/or systemic physiological and/or pharmacological effects.

The preferred form in which an agent is delivered generally determines the type of delivery system to be used, and vice versa. That is, the selection of a "passive" system which delivers the agent by diffusion or an electrically powered system which delivers the agent by electrotransport will be mostly determined by the form of the agent. For example, with passive delivery systems, it has generally been recognized that the agent is preferably delivered in either its free base or acid form, rather than in the form of a water soluble salt when the agent diffuses through the stratum corneum.

On the other hand, with electrotransport delivery devices, it has been recognized that the agents should generally be soluble in water. It is generally believed that the pathways for passive and electrotransported transdermal agent delivery through intact skin are different, with passive delivery occurring through lipid regions (i.e., hydrophobic regions) of the skin and electrotransport delivery occurring through hydrophilic pathways or pores such as those associated with hair follicles and sweat glands. For the case of pierced skin, substantial passive flux through the created pathways which are aqueous can be expected. The agent for passive delivery in the case of pierced skin is generally hydrophilic (e.g., water soluble salt form) and the preferred form of an agent for electrotransport delivery is also hydrophilic (e.g., water soluble salt form). For passive delivery, a combination of ionized agent (e.g., water soluble) and unionized agent (e.g., hydrophilic) can be used.

For osmotic and pressure driven systems which deliver agents by connective flow carried by a solvent, the agent preferably has sufficient solubility in the carrier solvent. It will be appreciated by those working in the field that the present invention can be used in conjunction with a wide variety of osmotic and pressure driven systems, as the invention is not limited to a particular device in this regard. For examples of osmotic and pressure driven devices, reference may be had to U.S. Pat. No. 4,340,480 to Eckenhoff, U.S. Pat. No. 4,655,766 to Theeuwes et al., U.S. Pat. No. 4,753,651 to Eckenhoff, U.S. Pat. No. 5,279,544 to Gross et al., U.S. Pat. No. 4,655,766 to Theeuwes, U.S. Pat. No. 5,242,406 to Gross et al., and U.S. Pat. No. 4,753,651 to Eckenhoff any of which can be used with the present invention.

This invention has utility in connection with the delivery of agents within any of the broad class of drugs normally delivered through body surfaces and membranes, including skin. In general, this includes drugs in all of the major therapeutic areas including, but not limited to, anti-infectives such as antibiotics and antiviral agents, analgesics including fentanyl, sufentanil, buprenorphine and analgesic combinations, anesthetics, anorexics, antiarthritics, antiasthmatic agents such as terbutaline, anticonvulsants, antidepressants, antidiabetic agents, antidiarrheals, antihistamines, anti-inflammatory agents, antimigraine preparations, antimotion sickness preparations such as scopolamine and ondansetron, antinauseants, antineoplastics, antiparkinsonism drugs, antipruritics, antipsychotics, antipyretics, antispasmodics, including gastrointestinal and urinary anticholinergics, sympathomimetrics, xanthine derivatives, cardiovascular preparations including calcium channel blockers such as nifedipine, beta-blockers, beta-agonists such as dobutamine and ritodrine, antiarythmics, antihypertensives such as atenolol, ACE inhibitors such as ranitidine, diuretics, vasodilators, including general, coronary, peripheral and cerebral, central nervous system stimulants, cough and cold preparations, decongestants, diagnostics, hormones such as parathyroid hormone, bisphophoriates, hypnotics, immunosuppressives, muscle relaxants, parasympatholytics, parasympathomimetrics, prostaglandins, psychostimulants, sedatives and tranquilizers.

The invention is also useful in the transdermal delivery of proteins, peptides and fragments thereof, whether naturally occurring, chemically synthesized or recombinantly produced. The invention may additionally be used in conjunction with the delivery of nucleotidic drugs, including oligonucleotide drugs, polynucleotide drugs, and genes. These substances typically have a molecular weight of at least about 300 daltons, and more typically have a molecular weight of at least about 300 to 40,000 daltons. Specific examples of peptides and proteins in this size range include, without limitation, LHRH, LHRH analogs such as goserelin, buserelin, gonadorelin, napharelin and leuprolide, GHRH, GHRF, insulin, insultropin, calcitonin, octreotide, endorphin, TRH, NT-36 (chemical name: N-[[(s)-4-oxo-2-azetidinyl]carbonyl] -L-histidyl-L-prolinamide), liprecin, pituitary hormones (e.g., HGH, HMG, desmopressin acetate, etc), follicle luteoids, αANF, growth factors such as growth factor releasing factor (GFRF), βMSH, GH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, HCG, hirulog, hyaluronidase, interferon, interleukins, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, bradykinin antagonists, ceredase, CSI's, calcitonin gene related peptide (CGRP), enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonists analogs, alpha-1 antitrypsin (recombinant), and TGF-beta.

Figure 10:
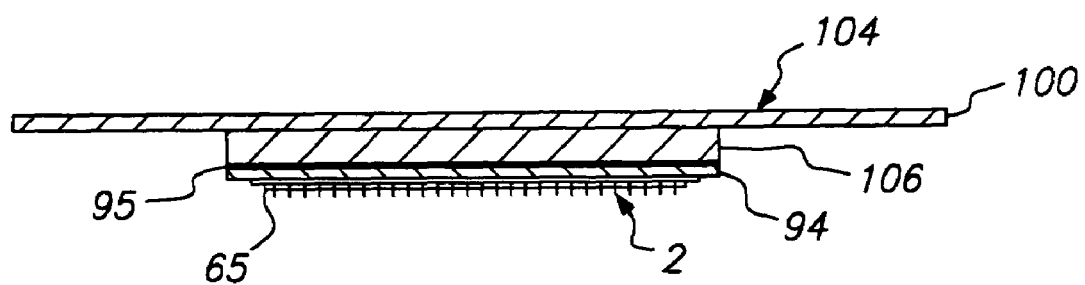
FIG. 10 is a diagrammatic cross-sectional view of an osmotic sampling system in accordance with one embodiment of the present invention.

As mentioned, the device 2 of the present invention can also be used with sampling devices including, but not limited to, reverse electrotransport (i.e., iontophoresis and/or electroosmosis), osmosis, and passive diffusion. FIG. 10 illustrates an osmotic sampling device 104 in combination with any of the embodiments described previously for device 2 with connecting medium 65. Osmotic sampling devices can be used to sample any of a variety of agents through a body surface including, but not limited to glucose, electrolyte, alcohol and illicit substances (e.g., drugs of abuse). The osmotic sampling device 104 is attached to a body surface by means of a flexible adhesive overlay 100. Device 104 is comprised of a salt layer 106 separated by semi-permeable membrane 95 from a layer 94 which stores the agent to be sampled. The layer 94 is absorbant in character in that the layer (e.g., hydrogel) passes fluid drawn through the body surface but retains the agent being sampled. The device 2 with connecting medium 65 thereon is in contact with layer 94 such that the projections on device 2 pierce the body surface and the connecting medium 65 makes good contact with the body surface. The salt layer 106 draws fluid from the body by osmosis through the connecting medium 65 and layer 94. The fluid drawn from the body contains the agent being sampled. As the fluid containing the agent passes through layer 94, the agent is retained in layer 94 and the fluid is absorbed by the salt layer 106. Preferably, the salt layer is free to expand or is encapsulated in a semi-permeable membrane 95 so that it retains the fluid therein. The sampled agent can be measured in situ directly or withdrawn from the layer 94 and sampled by conventional means.

Alternatively, salt layer 106, layer 94 and semi-permeable membrane 95 can be combined in one layer of absorbant hydrogel that stores the absorbed fluid as well as the agent sampled. Additionally, this one layer can be configured as the connecting medium 65 thereby greatly simplifying the device.

The following example is merely illustrative of the present invention and should not be considered as limiting the scope of the invention in any way, as this example and other equivalents thereof will become apparent to those versed in the art and in light of the present disclosure, drawings, and the accompanying claims.

EXAMPLE 1

The effect of the present invention is evaluated for its effect on drug flux and the skin resistance of a hairless guinea pig during electrotransport delivery of a model decapeptide drug. The following are specifications for the device. The device consists of a member having a plurality of rectangular openings having two blades, one on each end of a 0.25 mm$^2$ void area for each opening. The openings are aligned in pairs with every other pair of openings oriented 90 degrees to the previous pair of openings. All of the blades are about 500 micrometers long. There are 256 void areas per cm$^2$ and 512 blades per cm$^2$. An electrotransport system is used which applies a constant current of 0.1 mA/cm$^2$. It consists of a cathode counter reservoir comprising a Dulbelco's phosphate buffered saline imbibing gel and a donor anode reservoir comprising a hydroxyethylcellulose gel containing an aqueous solution of decapeptide bufferred at pH 7.5. The electrotransport system is placed on the skin of a lightly anesthetized hairless guinea pig. Decapeptide flux is evaluated by measuring urinary excretion of this peptide. Use of the present invention results in increased decapeptide flux over the transport period compared to an ordinary electrotransport device.

It will be appreciated by those of ordinary skill in the art that the invention can be embodied in other specific forms without departing from the spirit or essential character thereof. The presently disclosed embodiments are therefore considered in all respects to be illustrative and not restrictive. The scope of the invention is indicated by the appended claims rather than the foregoing description, and all changes which come within the meaning and range of equivalents thereof are intended to be embraced therein.

What is claimed is:

1. A method for introducing an agent through a body surface, comprising the steps of:
   providing a member having a body surface proximal side, a body surface distal side, a first surface on the body surface proximal side of the member and a second-surface distal side of the member; said member having a plurality of protrusions extending from the first surface and extending towards the body surface and a connecting medium disposed on at least a portion of the first surface;
   introducing the agent in the connecting medium;
   piercing the body surface with the plurality of protrusions extending from the first surface of the member;
   contacting the body surface with the connecting medium; and
   passing the agent through the body surface.

2. The method of claim 1 wherein the passing step comprises:
   administering the agent by a method selected from the group consisting of electrotransport, passive delivery, osmosis, and pressure.

3. A method for withdrawing an agent through a body surface, comprising the steps of:
   piercing the body surface with a plurality of protrusions extending from a body surface proximal side of a member having a connecting medium capable of passing the agent therethrough, the connecting medium disposed on at least a portion of the body surface proximal side;

contacting the body surface with the connecting medium; and withdrawing the agent through the body surface.

4. The method of claim 3 wherein the withdrawing step comprises: withdrawing the agent by a method selected from the group consisting of reverse electrotransport, passive sampling, and osmosis.

5. A device for introducing or withdrawing an agent through a body surface, comprising:
   a member having a body surface proximal side, a body surface distal side and a plurality of protrusions extending from said body surface proximal side;
   a connecting medium capable of storing the agent therein or passing the agent therethrough on at least a portion of the body surface proximal side of the member; and
   a sampling device connected to the body surface distal side, the sampling device selected from the group consisting of a reverse osmosis device, an electrotransport device, a passive device and an osmotic device.

6. A device for introducing or withdrawing an agent through a body surface, comprising:
   a member having a body surface proximal side, a body surface distal side and a plurality of protrusions extending from said body surface proximal side; said member further having at least one hole through the member;
   a connecting medium capable of storing the agent therein or passing the agent therethrough on at least a portion of the body surface proximal side of the member; and
   a sampling device connected to the body surface distal side, the sampling device selected from the group consisting of a reverse osmosis device, an electrotransport device, a passive device and an osmotic device.

* * * * *